United States Patent [19]

Pechhold

[11] 3,981,766

[45] Sept. 21, 1976

[54] METHOD OF CONTROLLING FUNGI AND BACTERIA IN PAPER PRODUCTS

[75] Inventor: Engelbert Pechhold, Chadds Ford, Pa.

[73] Assignee: E. I. Du Pont de Nemours and Company, Wilmington, Del.

[22] Filed: Feb. 21, 1975

[21] Appl. No.: 551,961

[52] U.S. Cl. ............................ 162/161; 106/15 R; 252/8.5 C; 252/8.55 D; 252/106; 424/316; 424/325
[51] Int. Cl.² ...................... D21D 3/00; D21H 5/22
[58] Field of Search ............. 162/161; 424/316, 325

[56] References Cited
UNITED STATES PATENTS

| | | | |
|---|---|---|---|
| 3,283,002 | 11/1966 | Brake | 260/563 |
| 3,299,136 | 1/1967 | Brown et al. | 260/563 C |
| 3,551,485 | 12/1970 | Raff et al. | 260/563 D |

FOREIGN PATENTS OR APPLICATIONS

| | | | |
|---|---|---|---|
| 1,165,930 | 3/1964 | Germany | 424/325 |

*Primary Examiner*—Dale R. Ore

[57] ABSTRACT

Various substituted cyclohexylamines, e.g., 4-aminodicyclohexylmethane, have demonstrated bacteriostatic and fungistatic properties and can be used as industrial biocides.

9 Claims, No Drawings

METHOD OF CONTROLLING FUNGI AND BACTERIA IN PAPER PRODUCTS

BACKGROUND OF THE INVENTION

There is a continuing need for effective biocides for industrial applications, e.g., compounds demonstrating biocidal properties for use in cooling water, secondary oil recovery, paper manufacture and in paints.

Aliphatic amines such as fatty amines are known in the art to have biocidal activity. Of the alicyclic amines, cyclohexylamine is known to control *thiobacillus ferrooxidans* and other organisms.

SUMMARY OF THE INVENTION

Substituted cyclohexylamines of the following formula, as well as their halogen, sulfate, nitrate or acetate salts, have demonstrated superior biocidal properties, e.g., bacteristatic and fungistatic properties:

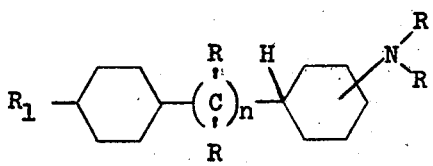

where R is hydrogen or methyl, preferably hydrogen, $R_1$ is hydrogen or

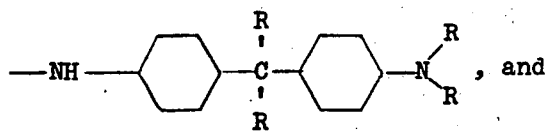

$n$ is 0 or 1, preferably 1.

Preferred within the above formula in view of their ease of manufacture and activity are 4-aminodicyclohexylmethane, 4,4'-[(iminobis)-1,4-cyclohexylidene dimethylene]dicyclohexylamine, their acetate salts and mixtures of these compounds or their acetate salts.

In some embodiments the salts of the above substituted cyclohexylamines offer the additional advantage of being corrosion inhibitors.

DESCRIPTION OF THE INVENTION

The substituted cyclohexylamines of the invention are known compounds and can be prepared by methods known in the art. Thus, they can be prepared by the methods disclosed in British Pat. No. 764,633 or U.S. Pat. Nos. 2,511,028; 3,636,108 and 3,644,522.

In these prior art processes the corresponding aromatic compound is hydrogenated by admixing the compound with hydrogen at a hydrogen partial pressure of at least 200 psi and a total pressure of from 200 to 15,000 psi. The temperature of the hydrogenation can range from 100°C to 300°C and is conducted in the presence of 0 to 200% by weight (based on the weight of compound to be hydrogenated) of ammonia. The preferred hydrogenation catalyst for use is metallic ruthenium supported on an inert carrier. The catalyst is preferably alkali moderated with from 0.1 to 15% of a basic metal compound calculated as the alkali metal and is present in amounts of 0.001% to 10% by weight based on the compound to be hydrogenated. Further details on the process can be found in the above-identified patents.

The following is an illustration of how the compounds of the invention can be prepared.

EXAMPLE 1 — 4-Aminodicyclohexylmethane

In a steel autoclave fitted with a stirring apparatus and a product draw off system retaining the catalyst in the reactor can be placed 200 parts of 4-aminodiphenylmethane as described in British Patent 764,633 and 100 parts of a finely divided 5% ruthenium on an alumina support and 15 parts of potassium methoxide. The mixture within the autoclave can then be heated to 290°C with stirring and hydrogen added to maintain a pressure of 290 atmospheres for 20 minutes. The resulting mixture can then be freed of catalyst by filtration and distilled to strip off solvent. Final distillation under vacuum can then be used to provide the desired product, 4-aminodicyclohexylmethane, which is a colorless viscose liquid.

Furthermore, the preferred compounds of the invention in the free form or their acetate salts can be obtained as byproducts during the manufacture of bis(4-aminocyclohexyl)methane. The following is an example of this process.

EXAMPLE 2

Catalytic reduction of bis(4-aminophenyl)methane as described in U.S. Pat. Nos. 2,511,028; 3,636,108 or 3,644,522 can be carried out at 100°–300°C and a hydrogen pressure of 200–15,000 psi in the presence of ruthenium catalyst on alumina. The resulting mixture is then freed of the catalyst by filtration and distilled under reduced pressure to give the fully saturated mixture of isomers of bis(4-aminocyclohexyl)methane. The distillation low boilers, 1 to 4% of the total product, will mainly consist of 4-aminodicyclohexylmethane, formed from bis(4-aminocyclohexyl)methane by cleavage of one amino group. The distillation residue, which makes up 1 to 20% of the total product, will consist of polyamine condensation products, mainly 4,4'-[(iminobis)-1,4-cyclohexylidene dimethylene]-dicyclohexylamine, a white solid.

Salts of the free amines of this invention can also be formed by contacting the amine with the appropriate acid in a solvent, e.g., water and either collecting the salt by filtration or by evaporation of the solvent. If the amine is a solid, it can be melted and the salt formed by adding the acid in water.

UTILITY

The compounds of the invention are highly effective fungistats and bacteriostats, i.e., they inhibit the growth of a broad spectrum of bacteria and fungi without necessarily destroying them.

The biocides of the invention are useful in many applications and are particularly useful in industrial applications such as commercial cleaners, paper and pulp manufacture, cooling water, secondary oil recovery, paints and the like. These utilities and the amounts of the compound to be used, i.e., the biocidally effective amount, will be discussed in greater detail in the following paragraphs.

Biocides are often added to paints to protect the paint while it is in the can. Thus, the biocides of this invention can be dispersed in a film former solution or suspension in amounts ranging from 0.01% to 1.0%. The film former can be any paint, enamels, lacquers or varnish, e.g., latex paints, acrylic paints, alkyd paints, vinyl acrylic paints, alkyd modified acrylics, etc. They are particularly useful with water base paints.

Biocides are useful in cooling waters to control the growth of bacteria, fungi and algae which tend to plug screens, filters, and pipe lines and interfere with heat transfer in process equipment. The biocides of the invention, preferable as aqueous solutions of their acetate salts, can either be applied to such cooling waters continuously at low dosage rates (5–100 ppm) or administered in shock treatment dosages (100–10,000 ppm). Formulations with other well known biocides can be used to intensify the degree of potency.

Slime-forming microorganisms can cause severe problems in the manufacture of pulp and paper and thus are responsible for significant losses in production and in the quality of the product. Biocides are used in many stages of papermaking. The biocides of this invention are useful in the various stages of the papermaking process, particularly when applied as aqueous solutions of the acetate salts. Dosage will vary for each individual paper or pulp mill. The average mill dosage can range from 1.5 oz. to 20 lb. per ton based on total paper production. The biocides of this invention can be successfully formulated with well known commercial biocides such as quaternary ammonium salts, triazines, chlorinated phenols, or organic tin compounds.

Biocides can be used effectively in the production of crude petroleum, e.g., in the secondary oil recovery by water flooding and in the preservation of drilling muds. The growth of bacteria in secondary recovery water causes operational difficulties and ultimately a decrease in oil production. The biocides of this invention can be administered to the recovery waters once or twice a day as a slug treatment at a dosage of 1 oz. to 5 lb. per 1,000 gal. of brine.

The biocides of the invention can be formulated in various ways for use, the particular manner being dependent upon the end use and the physical form of the biocide. In some embodiments the biocide is a liquid, thus no particular formulation is necessary. In other embodiments, e.g., the acetate salts, the biocide is water soluble, thus again no particular formulation is required for most end uses. When the biocide is a solid and not or only slightly soluble in water, it can be emulsified or dispersed in a suitable liquid diluent using conventional techniques.

The following examples illustrate the biocidal activity of the compounds of the invention.

EXAMPLE 3

The test procedure employed is the standard microbiological test tube liquid serial dilution method for determining susceptibility to antibiotics. (Bailey, W. R., and Scott, E. G., 1962. Diagnostic Microbiology, A Testbook for the Isolation and Identification of Pathogenic Microorganisms. The C. V. Mosby Publ. Co., St. Louis, Mo., pp 250–253.)

The tests were conducted as follows:

Ten mg of the compounds were mixed with 10 ml of sterile, distilled water containing 1.0 ml of dimethylformamide and one drop of Tween 80 surfactant. Appropriate dilutions were made from this solution in sterile, distilled water. Test compound concentrations were made by adding one ml of a diluted solution to 1 ml of sterile double-strength Difco (Difco Laboratories, Detroit, Michigan) brain-heart infusion broth (without PAB) in plugged test tubes.

The final test concentrations of 500 mcg, 200 mcg, 100 mcg, 50 mcg, 20 mcg and 10 mcg of compound per ml of culture medium were aseptically inoculated with two drops of an overnight broth culture of the following test bacteria:

Gram — Positive
  Bacillus subtilis
  Staphylococcus aureus
Gram — Negative
  Escherichia coli
  Pseudomomas aeruginosa
  Aerobacter aerogenes After incubation for 48 hours at 37°C, the test tubes were observed for signs of growth (turbidity). The lowest compound concentration tested which inhibited the bacterial growth (tubes remained clear) was recorded as the minimal inhibitory concentration (M.I.C.).

The overall efficacy against the five microorganisms is indicated in the following table.

| IN VITRO ANTIBACTERIAL ACTIVITY IN BRAIN-HEART INFUSION CULTURE BROTH | |
|---|---|
| Type of Compound | Overall M.I.C. (mcg/ml) After 48 Hours at 37°C |
| ⬡—⬡—NH₂ | 200 |
| ⬡—⬡ (H₂N-) | 200 |
| ⬡—CH₂—⬡—NH₂ cis & trans | 100 |
| ⬡—CH₂—⬡—NH₂·HCl cis & trans | 100 |
| ⬡—CH₂—⬡—NH₂·CH₃CO₂H cis & trans | 100 |
| ⬡—CH₂—⬡—NH₂ 75% cis | 200 |
| ⬡—CH₂—⬡—NH₂ trans | 100 |

-continued

IN VITRO ANTIBACTERIAL ACTIVITY IN BRAIN-HEART INFUSION CULTURE BROTH

| Type of Compound | Overall M.I.C. (mcg/ml) After 48 Hours at 37°C |
|---|---|
| ⟨⟩–CH(CH₃)–⟨⟩–NH₂ | 200 |
| ⟨⟩–C(CH₃)₂–⟨⟩–NH₂ | 50 |
| ⟨⟩–CH₂–⟨⟩–NH–CH₃ | 200 |
| ⟨⟩–CH₂–⟨⟩–N(CH₃)₂ | 500 |
| H₂N–⟨⟩–CH₂–⟨⟩–NH–⟨⟩–CH₂–⟨⟩–NH₂ · 3 HCl | 500 |

In the same test, cyclohexylamine gave an overall M.I.C. of above 500 mcg/ml.

EXAMPLE 4

The fungistatic properties of the compounds of this invention were tested by a modified agar-Petri plate technique. The compounds were added to potato dextrose agar on a w/w basis with concentrations expressed in parts per million (ppm). The test concentrations used were the following: 6,670 ppm; 2,400 ppm; 1,335 ppm; 935 ppm; 668 ppm and 400 ppm. Two widely occurring fungi were used in this test: Aspergillus niger and Pullularia pullulans. Inoculation was carried out by spraying the agar plates with the aqueous spore suspension of the two fungi. The plates were incubated for 14 days at a temperature of 28°C before being examined for fungal growth. The lowest compound concentration tested which inhibited the fungal growth was recorded as the minimal inhibitory concentration (M.I.C.).

The test results are shown in the following table.

| Test Compounds | M.I.C. in PPM (2 Weeks at 28°C) Aspergillus niger | Pullularia pullulans |
|---|---|---|
| ⟨⟩–CH₂–⟨⟩–NH₂ · CH₃CO₂H | 1,335 | <400 |
| ⟨⟩–CH₂–⟨⟩–NH₂ | 935 | <400 |

In the same test cyclohexylamine.HCl gave the following results:
Aspergillus niger >6,670 ppm
Pullularia pullulans >6,670 ppm.

I claim:
1. A method of controlling bacteria or fungi comprising applying to the locus to be protected a biocidally effective amount of a substituted cyclohexylamine of the formula:

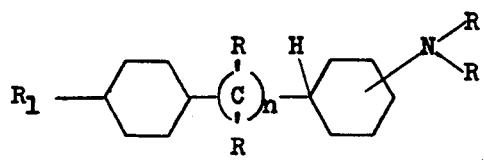

where R is hydrogen or methyl,
R₁ is hydrogen or

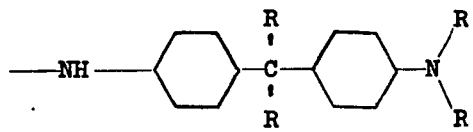

n is 0 or 1 and the halogen, sulfate, nitrate or acetate salt thereof.

2. The method of claim 1 wherein R is hydrogen, R₁ is hydrogen and n is 1.

3. The method of claim 1 wherein R is hydrogen, n is 1 and R₁ is

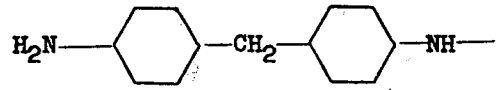

4. The method of claim 2 wherein the substituted cyclohexylamine is applied as the acetate salt.

5. The method of claim 3 wherein the substituted cyclohexylamine is applied as the acetate salt.

6. The method of claim 4 where the locus to be protected is cooling water.

7. The method of claim 5 where the locus to be protected is cooling water.

8. The method of claim 4 where the locus to be protected is a pulp or paper product.

9. The method of claim 5 where the locus to be protected is a pulp or paper product.

* * * * *